US006274329B1

(12) United States Patent
Struck

(10) Patent No.: US 6,274,329 B1
(45) Date of Patent: Aug. 14, 2001

(54) METHOD FOR THE DETECTING THYROID AUTOANTIBODIES

(75) Inventor: Joachim Struck, Berlin (DE)

(73) Assignee: B.R.A.H.M.S. Diagnostica GmbH, Berlin (DE)

( * ) Notice: Subject to any disclaimer, the term of this patent is extended or adjusted under 35 U.S.C. 154(b) by 0 days.

(21) Appl. No.: 09/380,732

(22) PCT Filed: Mar. 11, 1998

(86) PCT No.: PCT/EP98/01401

§ 371 Date: Nov. 23, 1999

§ 102(e) Date: Nov. 23, 1999

(87) PCT Pub. No.: WO98/40742

PCT Pub. Date: Sep. 17, 1998

(30) Foreign Application Priority Data

Mar. 12, 1997 (DE) ................................................ 197 10 211

(51) Int. Cl.⁷ ........................ G01N 33/53; G01N 33/537; G01N 33/543
(52) U.S. Cl. ......................... 435/7.1; 435/7.4; 435/7.93; 435/7.94; 435/7.95; 435/973; 436/506; 436/512
(58) Field of Search ................................. 435/7.1, 7.93, 435/7.4, 7.94, 7.95, 973; 436/506, 512

(56) References Cited

FOREIGN PATENT DOCUMENTS 2 265 713    10/1993   (GB).

OTHER PUBLICATIONS

Beever et al. Clinnical Chemistry 35(9):1949–1954, 1989.*
Nishikawa et al. J. of Endocrinology and Metabolism, 80(4):1461–1646, 1995.*
Mariotti et al. European J. of Immunology, 130(6):552–8, 1994.*

Chemical Abstracts, vol. 119, No. 19, Nov. 8, 1993, Columbus, Ohio, US; abstract No. 201596, XP002074219 siehe Zusammenfassung & J. Ruf et al; "Significance of thyroglobulin antibodies cross–reactive with thyroperoxidase (TGPO antibodies) in individual patients and immunized mice." Clinical and Experimental Immunology, Bd. 92, Nr. 1, 1993, pp. 65–72, Oxford UK Abstract only.

Chemical Abstracts, vol. 111, No. 19, Nov. 6, 1989, Columbus, Ohio, US; abstract No. 172028, XP002074222 siehe Zusammenfassung & K. Beever et al.: "Highly sensitive assays of autoantibodies to thyroglobulin and to thyroid peroxidase." Clinical Chemistry, Bd. 35, Nr. 9, 1989, pp. 1949–1954. Winston–Salem NC USA Abstract only.

* cited by examiner

*Primary Examiner*—David Saunders
*Assistant Examiner*—Amy DeCloux
(74) *Attorney, Agent, or Firm*—Pillsbury Winthrop LLP

(57) ABSTRACT

Method for the determination of thyroid autoantibodies Method for the determination of thyroid autoantibodies in a biological sample obtained from a patient in the differential diagnosis of diseases which are associated with changes of the thyroid and/or disturbances of the normal thyroid function, the determination of the presence and/or amount of the thyroid autoantibodies in the sample being effected with the use of an inmunodiagnostic assay method in which a test signal which represents overall the presence and amount of at least two antibodies, including anti-TPO autoantibodies and anti-Tg autoantibodies, in the sample is obtained per determination. The method increases the selectivity and sensitivity of the detection of the autoantibodies typical of specific autoimmune diseases while reducing the effort required.

7 Claims, No Drawings

METHOD FOR THE DETECTING THYROID AUTOANTIBODIES

This application is a national stage filing under 35 USC 371 from PCT/EP98/01401, filed Mar. 11, 1998.

The invention relates to a novel method for the determination of autoantibodies which are directed against thyroid autoantigens and are referred to below in short as "thyroid autoantibodies".

Among the diseases which are associated with disturbances of the normal function and/or with microscopically or optically perceptible changes of the thyroid, those which have the character of autoimmune diseases play an important role. The most well known thyroid diseases, which must be counted as autoimmune diseases, are in particular Graves' disease, Hashimoto's thyroiditis and primary hypothyroidism. Atrophic autoimmune thyroiditis, primary myxoedema, asymptomatic thyroiditis, postpartal thyroiditis and neonatal hypothyroidism may be mentioned as further such diseases, different designations being used for identical diseases or diseases of the same type, depending on the clinical picture.

The differential diagnosis demonstrating that the observed thyroid disease is one of the autoimmune diseases is based on the detection of autoantibodies in the patient. In many cases, the detection of these autoantibodies therefore permits the distinction of autoimmune diseases from other thyroid diseases by differential diagnosis (cf. Pfannenstiel, P. & Saller, B. in "Schilddrusenkrankheiten—Diagnose und Therapie" [Thyroid diseases—Diagnosis and Therapy], Berliner Medizinische Verlagsanstalt, 1993; or Ziegler, R., Pickardt, C. R., Willig, R.-P. in "Rationelle Diagnostik in der Endokrinologie" [Rational diagnosis in endocrinology], Georg Thieme Verlag, 1993). The known autoantibodies occurring in the case of thyroid autoimmune diseases belong to three different types which differ in the thyroid proteins acting as autoantigens. The three thyroid autoantigens are the TSH receptor, thyroperoxidase (TPO, identical to the earlier so-called microsomal antigen) and thyroglobulin (Tg) (Dawe, K., Hutchings, P., Champion, B., Cooke, A., Roitt, I., "Autoantigens in Thyroid diseases", Springer Semin. Immunopathol. 14, 285–307, 1993). Autoantibodies against the TSH receptor occur specifically in Graves' disease but not in other autoimmune diseases of the thyroid (Pfannenstiel & Saller, loc. cit.). In addition, autoantibodies against the other two autoantigens, i.e. against TPO and Tg, are also detectable with relatively low sensitivity in many cases in Graves' disease. For the diagnosis of Graves' disease, however, the detection of autoantibodies against TPO and/or Tg does not play a major role in view of the relevance and specificity of the detection of autoantibodies against the TSH receptor.

A determination of anti-TPO autoantibodies and anti-Tg autoantibodies is carried out in particular when autoimmune thyroiditis is suspected. In autoimmune thyroiditis of the Hashimoto type and in atrophic autoimmune thyroiditis, anti-TPO autoantibodies are very frequently present, but no autoantibodies against the TSH receptor. Frequently, the occurrence of anti-TPO autoantibodies is accompanied by anti-Tg autoantibodies, but there are cases where exclusively anti-Tg autoantibodies, but not anti-TPO autoantibodies, are detectable (Meng, W. in "Schilddrusenerkrankungen" [Thyroid diseases], Gustav Fischer Verlag, 1992; Pfannenstiel & Saller, loc. cit.; Ziegler et al., loc. cit.). Since there are therefore cases of autoimmune thyroiditis where no anti-TPO autoantibodies are detectable, the determination of anti-Tg autoantibodies is recommended in addition to the determination of anti-TPO autoantibodies (Feldt-Rasmussen, U. "Analytical and clinical performance goals for testing autoantibodies to thyroperoxidase, thyroglobulin, and thyrotropin receptor", Clinical Chemistry 42:1, 160–163, 1996). Whereas, apart from autoimmune thyroiditis of the Hashimoto type, there are further thyroid clinical pictures which constitute autoimmune diseases and in which anti-TPO or anti-Tg autoantibodies may be increased (primary myxoedema, asympotomatic thyroiditis, postpartal thyroiditis, neonatal hypothyroidism), there is only one indication in which anti-TPO autoantibodies do not occur alongside anti-Tg autoantibodies and are recommended for measurement, namely thyroid carcinoma (Feldt-Rasmussen, loc. cit.). In the case of thyroid carcinoma, large amounts of thyroglobulin are released from the thyroid cells, resulting in the formation of autoantibodies against Tg. Usually, thyroglobulin (Tg) is therefore determined for the detection of a thyroid carcinoma. However, the Tg determination may be disturbed by the presence of anti-Tg autoantibodies, and a so-called recovery measurement must therefore be carried out to back up the results of the measurements for the Tg determination. For confirming the findings in the case of a disturbed Tg detection, it may be of interest in specific cases to test the corresponding biological sample for the presence of anti-Tg autoantibodies.

The dominant method for the determination of autoantibodies when autoimmune thyroiditis is suspected is the determination of anti-TPO autoantibodies. The reliability of such determinations with respect to their diagnostic sensitivity is however under discussion (Haagen, U. & Bergmann, A., "Besondere Aspekte der Qualitatssicherung der Komponente Autoantigen bei Fertigreagenzien fur die Schilddrusenautoimmundiagnostik" [Particular aspects of the quality assurance of the component autoantigen in ready-to-use reagents for thyroid autoimmune diagnosis], Abstract from the "Jahrestagung der Sektion Schilddruse der Deutschen Gesellschaft fur Endokrinologie" [Annual Meeting of the Thyroid Section of the German Society for Endocrinology], Nov. 23–25, 1995, Hanover, pages 15–22): In the case of specific immunological assay methods for anti-TPO autoantibodies the antigen TPO is used as an assay component in a form in which all epitopes recognized by autoantibodies may not be present, it being possible in particular for conformational epitopes to be absent. This may be the case if a recombinant antigen produced by genetic engineering is used, if the antigen has been purified and hence conformationally stressed, if the antigen is immobilized directly on a solid phase and/or if the antigen is labelled under rigid conditions. Depending on the assay design it is also possible that specific significant anti-TPO autoantibodies are not detected (Mariotti, S., et al., "False negative results observed in anti-thyroid peroxidase autoantibody determination by competitive radioimmunoassays using monoclonal antibodies", Eur. J. Endocrinol. 130, 552–558, 1994).

Since cases are therefore known in which the sole determination of anti-TPO autoantibodies gives a false negative result, it is advisable to carry out an additional second determination, namely of anti-Tg autoantibodies, to confirm the diagnosis.

In spite of the advantages of an additional anti-Tg determination, the increasing pressure of costs in the health sector has led to discussions in which it has been suggested that an additional anti-Tg determination in the diagnosis of Hashimoto's thyroiditis be dispensed with although it is recognized that the danger of false diagnoses will be increased as a result (Nordyke, R. A. et al., "The superiority of antimicrosomal over antithyroglobulin antibodies for detecting Hashimoto's thyroiditis", Arch. Intern. Med. 153, 862–865, 1993).

Under these circumstances, it is the object of the present invention to provide a method for the determination of thyroid autoantibodies for the differential diagnosis of thyroid diseases, which method on the one hand requires only the relatively little effort of an individual determination but has a diagnostic sensitivity which reduces the risk of false negative results, at least compared with the determination of only one type of autoantibodies, and furthermore to provide at least one possibility for the successful technical implementation of such a method.

This object is achieved by a method according to the precharacterizing clause of patent claim 1, which is characterized in that an immunodiagnostic assay method is used in which a test signal which represents overall the presence and amount of at least two antibodies, including anti-TPO autoantibodies and anti-Tg autoantibodies, in the sample is obtained per determination.

Technical embodiments of such a method which are preferred at present are defined in more detail in subclaims 2 to 5. Claim 6 defines more exactly the indications for which, in the event of an appropriate suspicion, it is advantageous to carry out the method according to the invention.

The invention was based on the concept of systematically testing the extent to which a parallel detection of the two stated types of autoantibodies has demonstrable advantages over an individual determination of only one type of autoantibodies, and then establishing whether it is possible to detect two different types of autoantibodies, namely anti-TPO autoantibodies and anti-Tg autoantibodies, in biological samples, in particular patients' serum samples, in an individual determination simultaneously and without differentiating between the two types of autoantibodies. Given the possibility of reliable overall determination of the two autoantibodies, it was then furthermore necessary to establish the diagnostic sensitivity and specificity of such an overall determination in comparison with isolated determinations of anti-TPO and anti-Tg autoantibodies.

To test the above concept, a clinical trial was carried out in which the concentrations of anti-TPO autoantibodies and anti-Tg autoantibodies in serum samples of different groups of patients who suffered from thyroid diseases were determined, in each case alongside one another, in a conventional manner with the use of the commercial tests DYNOtest® anti-TPO$_n$ and DYNOtest® anti-Tg$_n$ of the Applicant B.R.A.H.M.S Diagnostica GmbH. The results of the pairs of single measurements were used for determining which concentrations of autoantibodies are obtained when the concentrations determined are summed. (Direct summation was chosen for the computational evaluation, but a suitable recalibration of the measured values is also possible in principle.) The commercial tests DYNOtest® anti-TPO$_n$ and DYNOtest® anti-Tg$_n$ each give, for the measured results obtained, cutoff values which serve for indicating that an investigated sample is autoantibody-positive when they are exceeded. For the determination of anti-TPO autoantibodies and of anti-Tg autoantibodies, a value of 60 mU/l is stated in each case. For taking into account the presence of both types of autoantibodies simultaneously, it is necessary to specify a new cutoff value, which was 73 mU/l in the trial.

In the case of said joint computational evaluation of the results of the individual determinations of the anti-TPO autoantibodies and anti-Tg autoantibodies, it was surprisingly found that, by a computational combination of the individual measurements, it is possible to achieve higher diagnostic sensitivity for the relevant patient groups than in the case of isolated determinations of anti-TPO autoantibodies or anti-Tg autoantibodies. In the case of the joint computational evaluation of the results of the individual measurements, it was found that essentially all samples which were measured either as anti-TPO autoantibody-positive or anti-Tg autoantibody-positive in individual determinations were also measured positive in each of the cases in an overall evaluation. Furthermore, it was found that the measured results were also specific in a joint evaluation, i.e. no false results were obtained for the normal group. The results for the various patient groups are summarized in Table 1. In Table 1, the column TOTAL contains the results of an overall evaluation of the pairs of individual measurements.

In a joint detection of the anti-TPO autoantibody concentrations and of the anti-Tg autoantibody concentrations, a diagnostic sensitivity which is better than that of isolated measurements of one of the stated concentrations is therefore obtained, while at the same time the specificity remains unimpaired.

TABLE 1

|  | n | aTPO > Cutoff | aTg > Cutoff | aTPO or aTg > Cutoff | TOTAL > Cutoff |
| --- | --- | --- | --- | --- | --- |
| Hashimoto, euthyroid | 208 | 84.1% | 65.4% | 90.4% | 90.4% |
| Hashimoto, juvenile, euthyroid | 33 | 51.5% | 36.4% | 57.6% | 57.6% |
| Hashimoto, under T4 | 53 | 92.5% | 67.9% | 96.2% | 96.2% |
| Graves' disease, untreated | 145 | 46.9% | 31.0% | 56.6% | 57.2% |
| Graves' disease, up to 6 months' treatment | 15 | 86.7% | 40.0% | 86.7% | 93.3% |
| Graves' disease, >6 months' treatment | 26 | 80.8% | 50.0% | 84.6% | 88.5% |
| Graves' disease, in remission | 17 | 70.6% | 41.2% | 76.5% | 76.5% |
| Graves' disease, after operation | 17 | 52.9% | 23.5% | 52.9% | 64.7% |
| Graves' disease, radio-iodine therapy | 11 | 81.8% | 36.4% | 81.8% | 81.8% |
| Goitre | 63 | 12.7% | 6.3% | 15.9% | 20.6% |
| Autonomy | 27 | 11.1% | 7.4% | 14.8% | 18.5% |
| Carcinomas | 102 | 20.6% | 11.8% | 28.4% | 26.5% |
| Normal group | 271 | 3.3% | 1.1% | 3.7% | 3.7% |

From the results of the computational evaluation of the test series described, the conclusion was drawn that it is not necessary to carry out two individual determinations to obtain reliable measured results but that, when it is technically possible to carry out an individual overall determination of both parameters (concentrations of the anti-TPO autoantibodies and anti-Tg autoantibodies), overall measured results which are superior to the individual measurements with regard to the diagnostic sensitivity would have to be obtained, while at the same time the specificity remains unimpaired. From the point of view of costs and also from the point of view of handling, the advantages of an overall individual measurement are striking: there is no need to carry out two tests; instead, a single test is sufficient. This considerably reduces the costs for material, personnel and equipment, leads to better handling characteristics and, owing to the reduction in the number of measurements to be carried out and the thereby reduced amount of test solutions need be disposed of, results in a more environmentally friendly determination. An inspection of the literature confirmed that there is no known indication of diagnostic or therapeutic importance that makes it necessary to differentiate whether anti-TPO autoantibodies or anti-Tg autoantibodies are raised. The overall determination thus leads to no loss of information compared with the practice to date.

To examine the question as to whether the conclusions drawn from a joint computational evaluation of individual determinations are correct even when an attempt is made to measure both parameters together in a single determination, i.e. to ensure that there is no mutual disturbance of the determinations of two types of autoantibodies and that it is possible to obtain an overall test signal which represents the total autoantibody concentration and guarantees the desired selectivity and sensitivity of the test, the overall test described in the following example was carried out.

In methods for the overall determination of the two types of autoantibodies, the procedure and principle is such that the immunodiagnostic assay method used comprises at least one step in which an optionally dilute liquid sample is reacted with at least two selective reagents, one of which selectively binds to anti-TPO autoantibodies and the other selectively binds to anti-Tg autoantibodies, the at least two selective reagents being used either for the selective separation of the anti-TPO autoantibodies and of the anti-Tg autoantibodies from the remainder of the liquid sample or for their selective labelling before or after their separation from the liquid phase.

The method used in the example can, in the general form, be described as a method which comprises the steps:

Binding of the antibodies present in the liquid sample, including the autoantibodies to be determined, to a solid phase by means of an unspecific binder bound to a solid phase, combined or sequential addition of two different tracer reagents which contain the same labelling component, one of the tracer reagents specifically labelling all bound anti-TPO autoantibodies and the other tracer reagent specifically labelling all bound anti-Tg autoantibodies, separation of the solid phase from the liquid reaction mixture and measurement of the tracer bound to the solid phase and recovery of a test signal which represents the sum of the amounts of the anti-TPO autoantibodies and anti-Tg autoantibodies in the sample.

A crude extract of human thyroids which contains human TPO in natural, undenatured form and in which the human TPO has been labelled or can be labelled by means of labelled antibody fragments without its binding capacity for anti-TPO autoantibodies being impaired is used, as described in the patent DE 41 20 412, as a tracer reagent for labelling anti-TPO autoantibodies.

EXAMPLE OF THE OVERALL DETERMINATION OF ANTI-Tg AND ANTI-TPO AUTOANTIBODIES

A novel test system in which the components of two commercial immunoprecipitation tests of the Applicant, B.R.A.H.M.S Diagnostica GmbH, were used was provided (HENNINGtest® anti-Tg and HENNINGtest® anti-TPO).

Both tests designed for the individual determinations of anti-Tg autoantibodies and anti-TPO autoantibodies operate with a protein A suspension as the solid phase. The antibodies present in the sample are bound unspecifically to the protein A suspension. In the individual determinations, the desired autoantibodies are then selectively radiolabelled with specific tracers, radiolabelled Tg being employed for labelling anti-Tg autoantibodies while anti-TPO autoantibodies are detected with the use of a crude thyroid membrane extract which contains natural TPO which has been selectively affinity-labelled with the aid of a radiolabelled Fab fragment of a monoclonal anti-TPO antibody.

In the trial, 130 different patient sera with different concentrations of anti-TPO autoantibodies and anti-Tg autoantibodies were measured in individual determinations according to the working instructions of the two stated commercial tests.

Also carried out was a combination test which was intended to serve as an overall determination of anti-TPO autoantibodies and anti-Tg autoantibodies and which gave only a single test signal.

For this purpose, 50 $\mu$l of protein A suspension were added to, in each case, 50 $\mu$l of the sample, which had been diluted beforehand according to the working instructions of the above tests. Thereafter, 50 $\mu$l of the tracer for detecting anti-TPO autoantibodies were added and, after 15 min, 50 $\mu$l of tracer for anti-Tg autoantibody detection were added to the same sample. After the addition of the two tracers, incubation was effected for 1 h at room temperature, 1 ml of buffer was added and the suspended solid phase was then separated from the test liquid by centrifuging, and the radioactivity bound to the solid phase was measured.

The measured results obtained are listed in Table 2. Table 2 shows the results of the measurements of the radioactivities bound to the isolated solid phase, stated in cpm, and the autoantibody concentrations (U/ml) calculated therefrom. Furthermore, Table 2 contains the total autoantibody concentrations calculated from the sums of the individual determinations (column Total aTPO+aTg). The signals obtained in the joint determination in the combination test (column COMBI) according to the example described were based on the calculated sums of the individual determinations. Those determinations which are rated clinically as autoantibody positive when said cutoff values of 100 U/ml are taken as a basis in each case for the individual determinations, and a cutoff corresponding to a radioactivity signal of 2900 cpm is taken as a basis for the combination test, are shown shaded.

The evaluation shows that the measured radioactivity signals obtained in the combination test for the individual samples are almost ideally the same as those calculated when the radioactivity signals of separate anti-TPO and anti-Tg determinations are summed. This result proves that an overall measurement of anti-Tg and anti-TPO autoantibodies is technically possible.

TABLE 2

| | anti-TPO | | anti-Tg | | Total aTOP + aTg | | COMBI | | COMBI/Total aTPO + aTg only values greater than 2000 cpm in COMBI |
|---|---|---|---|---|---|---|---|---|---|
| n | cpm | U/ml | cpm | U/ml | cpm | U/ml | cpm | | |
| 1 | 486 | 0 | 492 | 0 | 978 | 0 | 814 | 83% | |
| 2 | 536 | 0 | 455 | 0 | 991 | 0 | 1080 | 109% | |
| 3 | 593 | 0 | 429 | 0 | 1022 | 0 | 1009 | 99% | |
| 4 | 531 | 0 | 493 | 0 | 1024 | 0 | 822 | 80% | |
| 5 | 557 | 0 | 467 | 0 | 1024 | 0 | 1003 | 98% | |
| 6 | 560 | 0 | 482 | 0 | 1042 | 0 | 851 | 82% | |
| 7 | 588 | 0 | 458 | 0 | 1046 | 0 | 918 | 88% | |
| 8 | 513 | 0 | 544 | 0 | 1057 | 0 | 952 | 90% | |
| 9 | 469 | 0 | 589 | 0 | 1058 | 0 | 846 | 80% | |
| 10 | 564 | 0 | 507 | 0 | 1071 | 0 | 1104 | 103% | |
| 11 | 519 | 0 | 559 | 0 | 1078 | 0 | 961 | 89% | |
| 12 | 547 | 0 | 535 | 0 | 1082 | 0 | 850 | 79% | |
| 13 | 543 | 0 | 551 | 0 | 1094 | 0 | 898 | 82% | |
| 14 | 593 | 0 | 501 | 0 | 1094 | 0 | 988 | 90% | |
| 15 | 589 | 0 | 546 | 0 | 1135 | 0 | 865 | 76% | |
| 16 | 679 | 0 | 458 | 0 | 1137 | 0 | 752 | 66% | |
| 17 | 636 | 0 | 513 | 0 | 1149 | 0 | 1036 | 90% | |
| 18 | 668 | 0 | 485 | 0 | 1153 | 0 | 871 | 76% | |
| 19 | 546 | 0 | 620 | 0 | 1166 | 0 | 1069 | 92% | |
| 20 | 658 | 0 | 509 | 0 | 1167 | 0 | 887 | 76% | |
| 21 | 597 | 0 | 578 | 0 | 1175 | 0 | 826 | 70% | |
| 22 | 592 | 0 | 583 | 20 | 1175 | 20 | 1056 | 90% | |
| 23 | 708 | 0 | 489 | 0 | 1197 | 0 | 1140 | 95% | |
| 24 | 580 | 0 | 629 | 0 | 1209 | 0 | 817 | 68% | |
| 25 | 744 | 0 | 498 | 0 | 1242 | 0 | 1197 | 96% | |
| 26 | 529 | 0 | 769 | 6 | 1298 | 6 | 1090 | 84% | |
| 27 | 594 | 0 | 707 | 0 | 1301 | 0 | 1226 | 94% | |
| 28 | 779 | 0 | 526 | 0 | 1305 | 0 | 880 | 67% | |
| 29 | 718 | 0 | 605 | 0 | 1323 | 0 | 952 | 72% | |
| 30 | 515 | 0 | 817 | 13 | 1332 | 13 | 847 | 64% | |
| 31 | 531 | 0 | 802 | 11 | 1333 | 11 | 894 | 67% | |
| 32 | 670 | 0 | 717 | 0 | 1387 | 0 | 972 | 70% | |
| 33 | 826 | 0 | 625 | 0 | 1451 | 0 | 991 | 68% | |
| 34 | 1014 | 5 | 459 | 0 | 1473 | 5 | 888 | 60% | |
| 35 | 631 | 2 | 792 | 66 | 1473 | 68 | 1047 | 71% | |
| 36 | 967 | 3 | 516 | 0 | 1483 | 3 | 811 | 55% | |
| 37 | 930 | 2 | 554 | 0 | 1484 | 2 | 843 | 57% | |
| 38 | 1072 | 7 | 412 | 0 | 1484 | 7 | 907 | 61% | |
| 39 | 889 | 0 | 599 | 0 | 1488 | 0 | 792 | 53% | |
| 40 | 677 | 0 | 815 | 71 | 1492 | 71 | 1068 | 72% | |
| 41 | 563 | 0 | 939 | 31 | 1502 | 31 | 997 | 66% | |
| 42 | 698 | 0 | 804 | 11 | 1502 | 11 | 1248 | 83% | |
| 43 | 955 | 3 | 583 | 0 | 1538 | 3 | 912 | 59% | |
| 44 | 612 | 0 | 931 | 30 | 1543 | 30 | 1096 | 71% | |
| 45 | 924 | 1 | 658 | 0 | 1582 | 1 | 1147 | 73% | |
| 46 | 652 | 0 | 948 | 32 | 1600 | 32 | 850 | 53% | |
| 47 | 1090 | 8 | 515 | 0 | 1605 | 8 | 1009 | 63% | |
| 48 | 756 | 0 | 872 | 21 | 1628 | 21 | 994 | 61% | |
| 49 | 624 | 0 | 1030 | 44 | 1654 | 44 | 799 | 48% | |
| 50 | 1065 | 7 | 608 | 0 | 1673 | 7 | 817 | 49% | |
| 51 | 1150 | 10 | 551 | 0 | 1701 | 10 | 912 | 54% | |
| 52 | 1493 | 22 | 562 | 0 | 2055 | 22 | 1610 | 78% | |
| 53 | 1943 | 39 | 586 | 0 | 2529 | 39 | 1981 | 78% | |
| 54 | 2256 | 53 | 627 | 0 | 2883 | 53 | 2133 | 74% | 74% |
| 55 | 2921 | 81 | 518 | 0 | 3439 | 81 | 2562 | 74% | 74% |
| 56 | 944 | 7 | 2946 | 347 | 3890 | 354 | 2923 | 75% | 75% |
| 57 | 4345 | 139 | 552 | 24 | 4897 | 163 | 4377 | 89% | 89% |
| 58 | 5706 | 220 | 452 | 0 | 6158 | 220 | 5668 | 92% | 92% |
| 59 | 6244 | 252 | 612 | 0 | 6856 | 252 | 6116 | 89% | 89% |
| 60 | 7452 | 330 | 585 | 0 | 8037 | 330 | 6613 | 82% | 82% |
| 61 | 7480 | 332 | 898 | 25 | 8378 | 357 | 7210 | 86% | 86% |
| 62 | 8186 | 383 | 554 | 0 | 8740 | 383 | 7747 | 89% | 89% |
| 63 | 7959 | 366 | 1053 | 48 | 9012 | 414 | 7458 | 83% | 83% |
| 64 | 6449 | 248 | 2781 | 325 | 9230 | 573 | 7252 | 79% | 79% |
| 65 | 8562 | 394 | 1325 | 141 | 9887 | 535 | 9242 | 93% | 93% |
| 66 | 8163 | 363 | 1844 | 205 | 10007 | 568 | 7469 | 75% | 75% |
| 67 | 8477 | 405 | 1816 | 207 | 10293 | 612 | 8084 | 79% | 79% |
| 68 | 9125 | 442 | 1209 | 126 | 10334 | 568 | 8744 | 85% | 85% |
| 69 | 8341 | 377 | 2913 | 342 | 11254 | 719 | 8469 | 75% | 75% |
| 70 | 10736 | 596 | 552 | 0 | 11288 | 596 | 9653 | 86% | 86% |

TABLE 2-continued

COMBI/Total aTPO + aTg

|   | anti-TPO | | anti-Tg | | Total aTOP + aTg | | COMBI | | only values greater than 2000 cpm |
|---|---|---|---|---|---|---|---|---|---|
| n | cpm | U/ml | cpm | U/ml | cpm | U/ml | cpm | | in COMBI |
| 71 | 11419 | 682 | 536 | 3 | 11955 | 685 | 10721 | 90% | 90% |
| 72 | 11630 | 686 | 663 | 0 | 12293 | 686 | 10365 | 84% | 84% |
| 73 | 12043 | 730 | 894 | 24 | 12937 | 754 | 11855 | 92% | 92% |
| 74 | 11673 | 689 | 1571 | 153 | 13244 | 842 | 11797 | 89% | 89% |
| 75 | 12775 | 894 | 512 | 2 | 13287 | 896 | 12795 | 96% | 96% |
| 76 | 13546 | 923 | 657 | 0 | 14203 | 923 | 13019 | 92% | 92% |
| 77 | 14208 | 1032 | 769 | 6 | 14977 | 1038 | 14321 | 96% | 96% |
| 78 | 13959 | 1122 | 1204 | 126 | 15163 | 1248 | 13887 | 92% | 92% |
| 79 | 15008 | 1431 | 634 | 34 | 15642 | 1465 | 15469 | 99% | 99% |
| 80 | 15498 | 1677 | 528 | 7 | 16026 | 1684 | 15746 | 98% | 98% |
| 81 | 15772 | 1410 | 484 | 0 | 16256 | 1410 | 16063 | 99% | 99% |
| 82 | 15889 | 1449 | 552 | 0 | 16441 | 1449 | 14670 | 89% | 89% |
| 83 | 15888 | 1834 | 1015 | 101 | 16903 | 1935 | 16238 | 96% | 96% |
| 84 | 16711 | 2454 | 498 | 0 | 17209 | 2454 | 16889 | 98% | 98% |
| 85 | 16701 | 2451 | 596 | 23 | 17297 | 2474 | 16443 | 95% | 95% |
| 86 | 16987 | 2897 | 670 | 38 | 17657 | 2935 | 17343 | 98% | 98% |
| 87 | 16748 | 1845 | 1299 | 93 | 18047 | 1938 | 17034 | 94% | 94% |
| 88 | 17223 | 2212 | 904 | 26 | 18127 | 2238 | 17058 | 94% | 94% |
| 89 | 17421 | 3411 | 1003 | 99 | 18424 | 3510 | 17249 | 94% | 94% |
| 90 | 14550 | 1278 | 3907 | 484 | 18457 | 1762 | 15635 | 85% | 85% |
| 91 | 18051 | 4863 | 581 | 18 | 18632 | 4881 | 18305 | 98% | 98% |
| 92 | 17800 | 4748 | 900 | 84 | 18700 | 4832 | 17935 | 96% | 96% |
| 93 | 929 | 7 | 18047 | 4221 | 18976 | 4228 | 14205 | 75% | 75% |
| 94 | 17834 | 4219 | 1212 | 126 | 19046 | 4345 | 17892 | 94% | 94% |
| 95 | 18214 | >Standard | 900 | 85 | 19114 | >Standard | 18558 | 97% | 97% |
| 96 | 18238 | 5639 | 908 | 84 | 19146 | 5723 | 17261 | 90% | 90% |
| 97 | 18456 | >Standard | 1188 | 124 | 19644 | >Standard | 19687 | 100% | 100% |
| 98 | 19007 | >Standard | 900 | 84 | 19907 | >Standard | 19456 | 98% | 98% |
| 99 | 18957 | >Standard | 1013 | 101 | 19970 | >Standard | 19904 | 100% | 100% |
| 100 | 19623 | >Standard | 428 | 0 | 20051 | >Standard | 19210 | 96% | 96% |
| 101 | 20045 | >Standard | 602 | 25 | 20647 | >Standard | 20015 | 97% | 97% |
| 102 | 15379 | 1291 | 5657 | 889 | 21036 | 2180 | 16281 | 77% | 77% |
| 103 | 19126 | 8690 | 1941 | 217 | 21067 | 8907 | 19218 | 91% | 91% |
| 104 | 20385 | >Standard | 1115 | 114 | 21500 | >Standard | 20150 | 94% | 94% |
| 105 | 18576 | >Standard | 2950 | 347 | 21526 | >Standard | 20781 | 97% | 97% |
| 106 | 18934 | 7829 | 2721 | 317 | 21655 | 8146 | 20569 | 95% | 95% |
| 107 | 19248 | 9249 | 2410 | 276 | 21658 | 9525 | 18091 | 84% | 84% |
| 108 | 18235 | 7399 | 3501 | 425 | 21736 | 7824 | 20125 | 93% | 93% |
| 109 | 18507 | 6276 | 3557 | 432 | 22064 | 6708 | 19834 | 90% | 90% |
| 110 | 6368 | 259 | 15935 | 3487 | 22303 | 3746 | 18326 | 82% | 82% |
| 111 | 19048 | 8510 | 3285 | 394 | 22333 | 8904 | 20224 | 91% | 91% |
| 112 | 19117 | 8610 | 3527 | 428 | 22644 | 9038 | 20840 | 92% | 92% |
| 113 | 19049 | >Standard | 3734 | 458 | 22783 | >Standard | 20734 | 91% | 91% |
| 114 | 19228 | 9203 | 4410 | 561 | 23638 | 9764 | 20235 | 86% | 86% |
| 115 | 21030 | >Standard | 2635 | 305 | 23665 | >Standard | 21836 | 92% | 92% |
| 116 | 14918 | 1479 | 9903 | 1593 | 24821 | 3072 | 18161 | 73% | 73% |
| 117 | 18288 | 5463 | 8334 | 1264 | 26622 | 6727 | 21911 | 82% | 82% |
| 118 | 19059 | >Standard | 7680 | 1256 | 26739 | >Standard | 23337 | 87% | 87% |
| 119 | 18294 | >Standard | 8710 | 1339 | 27004 | >Standard | 23732 | 88% | 88% |
| 120 | 17810 | 4226 | 10101 | 1636 | 27911 | 5862 | 21375 | 77% | 77% |
| 121 | 19706 | >Standard | 8969 | 1512 | 28675 | >Standard | 23214 | 81% | 81% |
| 122 | 13779 | 1079 | 17245 | 3848 | 31024 | 4927 | 23190 | 75% | 75% |
| 123 | 18189 | 5171 | 13980 | 2644 | 32169 | 7815 | 24809 | 77% | 77% |
| 124 | 18855 | 7619 | 13338 | 2452 | 32193 | 10071 | 27721 | 86% | 86% |
| 125 | 19532 | >Standard | 12773 | 2292 | 32305 | >Standard | 29698 | 92% | 92% |
| 126 | 17976 | 4624 | 14406 | 2773 | 32382 | 7397 | 25952 | 80% | 80% |
| 127 | 17562 | 3645 | 16145 | 3390 | 33707 | 7035 | 30835 | 91% | 91% |
| 128 | 18349 | 5785 | 18824 | 4648 | 37173 | 10433 | 32898 | 88% | 88% |
| 129 | 20162 | >Standard | 17368 | 3902 | 37530 | >Standard | 34829 | 93% | 93% |
| 130 | 22199 | >Standard | 23251 | >Standard | 45450 | >Standard | 42250 | 93% | 93% |
| | | | | | | | Mean value = | 83% | 89% |

The overall measurement described and involving the use of the components of the known immunoprecipitation tests represents only one possibility for the technical implementation of the overall determination of the two types of autoantibodies. The combination of other assay designs appears possible in a similar manner, and tests which operate according to other assay principles are also intended to be covered by the method according to the invention. In particular, the following may be mentioned:

A combined assay for the overall determination of anti-TPO and anti-Tg autoantibodies according to the competitive principle, as described, for example, in the patent DE 41

20 412. It is possible here to employ a mixed solid phase to which both selective anti-TPO antibodies and anti-Tg antibodies are bound. With the use of a tracer mixture which contains both radiolabelled Tg and TPO, the presence of the desired autoantibodies in the sample manifests itself as a reduction in amount of tracer bound to the solid phase in comparison with an autoantibody-free sample. When Tg is present in the TPO preparations used, it might be necessary to separate off said Tg by known methods, such as, for example, affinity chromatography or other chromatographic methods. The desired technical sensitivity can be established by means of suitable amounts of solid-phase antibodies and tracers, and the reliability of the measured results is ensured by suitable calibration measures.

A combined assay with immobilized antigens can also be realized. The antigens Tg and TPO would be immobilized on a solid phase directly or by means of suitable preimmobilized anti-Tg and anti-TPO antibodies. The anti-Tg and anti-TPO autoantibodies bound after reaction with the patient's sample can be detected, for example, with labelled protein A or labelled anti-human-IgG for obtaining an overall test signal.

A combined assay which makes use of the bivalence of the antibodies to be measured is also possible. For this purpose, the antigens Tg and TPO could be immobilized on a solid phase directly or by means of suitable preimmobilized selective anti-Tg and anti-TPO antibodies. The anti-Tg and anti-TPO autoantibodies bound to the patient's sample after the reaction can then be detected by a tracer mixture which contains both radiolabelled Tg and radiolabelled TPO. In this case, too, Tg fractions present in the TPO preparation could be separated off by the above-mentioned known chromatographic methods.

Further assay designs known per se are possible. The assay variants listed above were singled out because they are currently of particular importance for the routine determination of anti-Tg autoantibodies and anti-TPO autoantibodies.

In the assay variants described above, it was furthermore assumed that the reagents used as tracers contain the same labelling component so that an overall single test signal can be obtained. However, this does not rule out the possibility of at least one of the reagents containing a further labelling component which makes it possible, with the use of the same test solution, also individually to measure one of the autoantibodies to be determined, in addition to the overall determination. In an assay system in which the tracers have different labelling components, it is as a rule not possible to obtain an overall test signal. With a suitable choice of tracers, such assays may however also have, in comparison with the conventional two separate measurements, the advantage that pipetting need be carried out only once for the preparation of the test solution and two measured results can be obtained with a single batch.

In the present description, only the joint detection of two specific autoantibodies, namely anti-TPO autoantibodies and anti-Tg autoantibodies, is described in detail. However, it is within the scope of the present invention to extend the method to cases where one or more further antibodies are also detected in the overall measurement, whether autoantibodies whose additional detection is diagnostically valuable or any added antibodies whose presence in the test solutions leads to a constant base signal which permits a further check of the correctness of the measurements or shifts the measuring range.

What is claimed is:

1. A method for the immunodiagnostic determination of the presence and amount of thyroid autoantibodies in a liquid biological sample obtained from a patient for the differential diagnosis of diseases which are associated with changes of the thyroid and/or disturbances of the normal thyroid function; said immunodiagnostic determination comprising contacting said biological sample with a test medium so that one common signal is produced, which signal represents the presence and the overall amount of at least two thyroid autoantibodies, comprising anti-TPO autoantibodies and anti-Tg autoantibodies, in said sample.

2. The method according to claim 1, wherein said immunodiagnostic determination comprises the step of reacting a liquid reaction mixture containing said liquid sample obtained from a patient with at least two selective binding reagents, one of those reagents selectively binding to anti-TPO autoantibodies and the other of said reagents selectively binding to anti-Tg autoantibodies, said at least two selective reagents, in said immunodiagnostic method, being used for either (i) the selective separation of both of the anti-TPO autoantibodies and the anti-Tg autoantibodies from the remainder of the liquid reaction mixture, or (ii) the selective labelling of both of the anti-TPO autoantibodies and the anti-Tg autoantibodies before or after their separation from the liquid reaction mixture.

3. The method according to claim 1, wherein said immunodiagnostic determination comprises the steps of:
   (i) obtaining a liquid sample of a body fluid from a patient showing changes of the thyroid and/or disturbances of the normal thyroid function,
   (ii) preparing a reaction system comprising a liquid reaction mixture comprising said liquid sample, and a solid phase carrying a nonspecific binder,
   (iii) binding antibodies present in said liquid reaction mixture, including the autoantibodies to be determined, to the nonspecific binder,
   (iv) adding, together or sequentially, two different tracer reagents which contain the same labeling component, one of said tracer reagents constituting a specific tracer for all anti-TPO autoantibodies bound to the nonspecific binder and the other of said tracer reagents constituting a specific tracer for all anti-Tg autoantibodies bound to the nonspecific binder,
   (v) separating the solid phase carrying the nonspecific binder from the liquid reaction mixture, and
   (vi) measuring the labeling component bound to the solid phase and obtaining one common test signal which represents the sum of the amounts of anti-TPO autoantibodies and anti-Tg autoantibodies in the sample.

4. The method according to claim 2, wherein the selective labeling of the anti-TPO autoantibodies is effected by using a crude extract of human thyroid which extract contains human TPO in natural, undenatured form and in which extract said human TPO previously was labeled by means of labeled selective antibody fragments not impairing the binding capacity of the human TPO of said crude extract to anti-TPO autoantibodies.

5. The method according to claim 2, wherein the selective labeling of the anti-TPO autoantibodies is effected by using a crude extract of human thyroid which extract contains human TPO in natural, undenatured form, said human TPO in said extract being selectively labeled in subsequent reaction step by means of labeled selective antibody fragments not impairing the binding capacity of said human TPO of said crude extract to anti-TPO autoantibodies.

6. The method according to claim 2, wherein the immunodiagnostic assay method is selected from a group consisting of an immunometric sandwich method, a competitive assay method and a method using a double antibody technique for separation and/or labeling.

7. The method according to claim 1, wherein the disease associated with changes of the thyroid and/or disturbances of the normal thyroid function is selected from the group consisting of an autoimmune thyroiditis of the Hashimoto type, an atrophic autoimmune thyroiditis, a primary myxoedema, an asymptomatic thyroiditis, a postpartal thyroiditis and a neonatal hypothyroidism, and the differential diagnosis is made on the basis of the evaluation of the common test signal representing a positive measurement for the presence of at least one of said anti-TPO autoantibodies and said anti-Tg autoantibodies, in combination with the case history and/or the clinical symptoms of the respective patient.

* * * * *